(12) United States Patent
Yue

(10) Patent No.: US 7,785,774 B2
(45) Date of Patent: Aug. 31, 2010

(54) ADJUSTABLE MOLECULAR MOTOR MICROPOWER BIOSENSOR AND ITS APPLICATION

(75) Inventor: Jiachang Yue, Beijing (CN)

(73) Assignee: Institute of Biophysics, Chinese Academy of Sciences, Beijing (CN)

( * ) Notice: Subject to any disclaimer, the term of this patent is extended or adjusted under 35 U.S.C. 154(b) by 427 days.

(21) Appl. No.: 11/721,881

(22) PCT Filed: Dec. 15, 2005

(86) PCT No.: PCT/CN2005/002195

§ 371 (c)(1),
(2), (4) Date: Jun. 15, 2007

(87) PCT Pub. No.: WO2006/063527

PCT Pub. Date: Jun. 22, 2006

(65) Prior Publication Data

US 2009/0275052 A1     Nov. 5, 2009

(30) Foreign Application Priority Data

Dec. 16, 2004    (CN) .................... 2004 1 0098929

(51) Int. Cl.
*C12Q 1/70*     (2006.01)

(52) U.S. Cl. .............. 435/5; 435/7.91; 435/287.1; 436/519; 436/532

(58) Field of Classification Search ............ None
See application file for complete search history.

(56) References Cited

U.S. PATENT DOCUMENTS

| | | | |
|---|---|---|---|
| 6,210,896 B1 | 4/2001 | Chan | |
| 6,989,235 B2 * | 1/2006 | Chapsky et al. | 435/6 |
| 2002/0034757 A1 * | 3/2002 | Cubicciotti | 435/6 |
| 2003/0134325 A1 * | 7/2003 | Cubicciotti | 435/7.1 |
| 2005/0089890 A1 * | 4/2005 | Cubicciotti | 435/6 |

FOREIGN PATENT DOCUMENTS

| | | |
|---|---|---|
| CN | 1513752 | 7/2004 |
| JP | 2004-301704 | 10/2004 |
| WO | WO 03/040302 | 3/2003 |

* cited by examiner

*Primary Examiner*—N. C. Yang
(74) *Attorney, Agent, or Firm*—Knobbe Martens Olson & Bear LLP

(57) ABSTRACT

A regulable molecular motor micropower biosensor comprises: a rotary motor, an optical energy conversion device, a signal molecular output device, a power resource system, a protective layer, a supporting material, and a bilayer lipid membrane fixing material. The molecular motor micropower biosensor is used for detecting biological macromolecules, viral molecules, etc.

8 Claims, 12 Drawing Sheets

(a) external fluorescence labeling (b) internal fluorescence labeling (A)

(B)

ADJUSTABLE MOLECULAR MOTOR MICROPOWER BIOSENSOR AND ITS APPLICATION

RELATED APPLICATIONS

This application is a U.S. National Phase of International Application No. PCT/CN2005/002195, filed Dec. 15, 2005, designating the U.S. and published not in English on Jun. 22, 2006 as WO 2006/063527, which claims the benefit of Chinese Application No. 200410098929.9, filed Dec. 16, 2004.

FIELD OF THE INVENTION

The present invention relates to the field of nanometer biosensor of the power engine of a nanoscale device. More particularly, the present invention relates to an adjustable molecular motor micropower biosensor. The present invention further relates to the use of the regulable molecular motor in the detection of biological macromolecules, viral molecules, etc.

DESCRIPTION OF THE PRIOR ART

Nowadays, technologies in fields such as electron device, chemical industry and life sciences have come into the era of nanoscience. Molecular motor is believed to be the growing point of new technologies such as nanomechanical materials due to its extraordinary functions. Because biomotors (power engines of nanoscale devices) and nanoscale devices can not work without energy supply, there is a need for micromotors in molecular-scale.

Some technological innovations are marked by newly discovered energy to mechanical work conversion. The invention of steam engine, for instance, triggered industrial revolution. Molecule motor (nanomotor) is a newly discovered energy conversion technology, which will definitely trigger another technology revolution comparable to the industrial revolution, bringing the whole humanity into a brand new epoch.

Currently, since nanomotor technology is far from mature, it is still not possible for researchers to produce nanoengine. Nevertheless, the nature has already provided us biological nanomotor which can perform specific function in high efficiency. The mechanism of how biomotors generate power has become one of the most exciting research fields for scientists.

F-ATPase molecular motor in biomembrane is a multi-subunit protein complex (see FIG. 1). The makeup of its transmembrane part (referred to as $F_0$-ATPase) is a:b:c=1:2:10-12; $F_1$-ATPase couples to $F_0$ outside the membrane. The makeup of $F_1$-ATPase molecular motor is a:$\beta$:$\gamma$:$\delta$:$\epsilon$=3:3:1:1:1. When protons flux from inside to outside of the membrane (outflux), they drives the rotation of the c-ring and hence the rotation of the $\gamma$ subunit of $F_1$ in clockwise. At the same time, ATP is synthesized from ADP and Pi at three catalytic sites on $F_1$. Conversely, during ATP hydrolysis, $\alpha_3\beta_3$ drives $\alpha_3\beta_3\gamma$, $\epsilon$ and hence c-ring of $F_0$ to rotate in counter-clockwise, resulting in the transport of protons from outside to the inside of the membrane (influx). As can be seen from the above description, $F_0F_1$-ATPase is a pair of reversible molecule machine. Under physiological conditions, $F_0F_1$-ATPase mainly carries out oxidative phosphorylation in mitochondria and photo-phosphorylation in photosynthesis bacteria, converting electron energy (or light energy) to proton gradient, and thereby driving ATP synthesis (*Trends in Biochemical Sciences*, volume 27, 2002, pages 154-160).

In 1997, scientists in Japan disclosed the smallest, fastest, and most efficient rotating motor at that time. Since then, many achievements were made by researchers all over the world (*J. Biol. Chem.*, 276:1665-1668, 2001). In one of the research achievements, fluorescent labeled protein filament (about 1-2 µM in length) was linked to $\gamma$ subunit of the molecular motor, the rotation of which was directly observed under fluorescence microscopy. However, because the protein filament (about 1-2 µM in length) is a too heavy load for the molecular motor which is only 10 nm in length, the sensitivity of the detection is low and difficult to regulate. Therefore, though promising, two major issues seriously impede the application and development of molecular motor: 1. lack of regulatory techniques for molecular motor; and 2. difficulties in expressing the signal of molecular motor rotation in high sensitivity.

DISCLOSURE OF THE INVENTION

After exhaustive study, the inventors of the present invention found that by using fluorescence probe as a sensitive signal sensor of the rotation of the molecular motor, the rotation signal of the molecular motor can be easily obtained without being linked to a heavy load. Antibody technology was further used to regulate the rotation function of the molecular motor. The invention also relates to the use of the fluorescence as a biological micropower sensor.

The basic concepts and principles will be described firstly as follows.

Rotary molecular motor, combined with immunological techniques, was used as a sensor in the present invention to detect chemical and biological substances. Conventional immunological biosensor and the immunological molecular motor rotary biosensor of the present invention are fundamentally different both in structure and in basic mechanisms. Although the two sensors have no difference in the mechanism of molecule recognition, there exits essential difference. In the mechanism of detecting conventional immunological biosensor can be called as static sensors, the signal of which depends mainly on "with/without" of an object to be tested. In contrast, rotary sensor can be called as dynamic sensors, the signal of which depends on the speed changes of the rotary motor.

Furthermore, a rotary biosensor assembles a molecule recognition and signal conversion device, as well as a bioactive element into a whole simple setup (see FIG. 11A). Fluorescence technology was used to detect the rotation speed of the motor. Linking of different loads (object to be tested) to the motor results in different rotation speeds. A variety of methods such as using chemical, light, outside force, etc. can be applied to regulate the rotation speed. The rotation time can be in seconds, minutes, hours, or even days (as desired). Because of the difference in the detection mechanism, the rotary sensor of the present invention not only has high sensitivity, but also high resolution. In addition, the rotary sensor of the present invention does not need special labeling, which saves time and is of importance in quick application process.

Mechanism of Molecule Detection

The rotation speed (fast/slow) is used to identify the antigen molecule captured (big/small, more/less, heavy/light). Where the molecule captured is more/big/heavy, the rotation speed of the molecular motor will become slower. Conversely, where the molecule captured is less/small/light, the rotation speed of the molecular motor will become faster.

Detection of the Rotation Speed of the Molecular Motor

The change of the fluorescence intensity is directly related to the rotation speed of the molecular motor, and the rotation speed is further related directly to the size/quantity of the molecule loaded. Therefore, the less the motor being loaded with the molecules, the faster the rotation speed of the motor. In such a case, the magnitude that fluorescence changes from week into strong becomes more dramatic and faster. On the other hand, the more/heavier the motor being loaded with the molecules, the slower the rotation speed of the motor. In such a case, the magnitude that the fluorescence changes from week into strong becomes less dramatic and slower. Accordingly, the rotation speed (fast/slow) of the motor and thus the loading situation of the motor can be determined from the magnitude changes of the fluorescence signal. Since the relationship between the magnitude changes of the fluorescence signal and the rotation process of the molecular motor is accumulative, even there is only relatively minor difference among the molecules loaded, a high detection accuracy can still be achieved.

Initiation and Regulation of the Rotation of the Molecular Motor

The application of the molecular motor requires a means to initiate and regulate its rotation speed: (a) by converting chemical energy to mechanical energy (e.g., ATP hydrolyzes into ADP and Pi, releasing energy at the same time; or protons transport through membrane to promote the synthesis of ATP from ADP and (b) converting light energy to electron energy (forming transmembrane potential gradient); (c) using outer force to drive the rotation of the molecular motor.

Molecule Motor and its Structure and Function $F_0F_1$-ATPase is an enzyme responsible for energy conversion in living bodies. It is composed of two parts, a water soluble part of $F_1$-ATPase and a transmembrane part of $F_0$-ATPase. With regard to structure, it also has two parts, a stator and a rotor, which indicates $F_0F_1$-ATPase is a rotary biomolecular motor. The stator is composed of $\alpha_3\beta_3\delta$ of $F_1$ and $ab_2$ of $F_0$, and the rotor is composed of $\gamma\epsilon$ of $F_1$ and $c_n$ of $F_0$. As the $F_0$ and $F_1$ coexist in one synthase, the coupling between two parts is very important for $F_0F_1$-ATPase functioning, and the two parts regulate reciprocally. Accordingly, when $F_1$ part (non-active part) is loaded, it will couple to the transmembrane part $F_0$-ATPase.

As the size of the load relates directly to the rotation speed of the c subunit of $F_0$ coupled to $\gamma\epsilon$, and the rotation speed of the c subunit of $F_0$ is coupled with the transport speed of protons, we can easily determine the loading situation of $F_1$ part with a fluorescence pH probe, which is used to test the transport speed of protons (as shown in FIG. 11A). Our pilot study has indicated the method is fast, sensitive, and easy to use.

The ultrasensitive molecule biosensor of the present invention has a molecular motor and has immunological recognition function, the mechanism of which is clear and reliable (see FIG. 11A).

Therefore, another object of the present invention is to provide a regulable molecular motor as a micropower biosensor, which comprises:

1. a rotary motor: $F_0F_1$-ATPase, as shown by reference marks 3 and 4 in FIG. 2;
2. an optical energy conversion device, consisting of light reaction center (RC) and a cold light source, as shown by reference mark 9 in FIG. 2;
3. an electron conversion device, which is in the same system of the optical energy conversion device, as shown by reference mark 11 in FIG. 2; given chromatophore as an example, it has a bilayer phosphatidase body with a diameter of about 30-60 nm; the chromatophore contains $F_0F_1$-ATPase and 6-11 RC light energy conversion complexes;
4. a signal molecular output device, consisting of light excitation and emitting device (as shown by reference mark 10 in FIG. 2), and a fluorescence probe (as shown by reference mark 5 in FIG. 2);
5. a power resource system, consisting of water, ATP, ADP, Pi, and visible light (as shown by reference mark 12 in FIG. 2);
6. a protective layer, which is a bilayer lipid membrane used as a functional protective layer (as shown by reference mark 6 in FIG. 2);
7. a supporting material and a fixing material for the bilayer lipid membrane, as shown by reference marks 7 and 8 in FIG. 2.

In a preferred embodiment of the present invention, the fluorescence probe is Lipids-fluorescein labeled outside of the membrane (DHPE, (Fluorescein (N-(fluorescein-5-thiocarbamoyl)-1,2-dihexadecanoyl-sn-glycero-3-phosphoethanolamine, trimethyl-ammonium salt) (Molecular Probes Co., USA, F362). Lipids-fluorescein can be labeled specifically to the outside of the membrane, and is extremely sensitive to pH changes (*Biochim. Biophys. Acta* 939:289, 17, *J. Phys. Chem.* 81:1755 (1977)). When the Lipids-fluorescein is labeled outside the cell membrane, ATPase hydrolysis causes $F_1$-ATP to rotate in counter-clockwise, and at the same time transports protons from the outside to the inside of the cell membrane, thereby increasing the pH value outside of the cell. As a result, the fluorescence signal of Lipids-fluorescein increases under light excitation. Conversely, the fluorescence signal of Lipids-fluorescein decreases. In another preferred embodiment of the present invention, the fluorescence probe is fluorescein (Molecular Probes Co., USA, F1300) labeled inside the membrane. When the fluorescein is specifically labeled inside the membrane, the rotation of the molecular motor causes the transport of protons from the outside to the inside of the cell membrane, thereby decreasing the pH value inside the cell. On the other hand, during ATP synthesis, protons are transported from the inside to the outside of the cell membrane, thereby increasing the pH value inside the cell, and a similar result can be obtained likewise. Therefore, by using the cell membrane unidirectional pH fluorescence probe technique, the florescence intensity and the rotation of the molecular motor (or referred to as proton transport capability) are related directly (as shown in FIG. 3).

In one embodiment of the present invention, the rotation of the molecular motor is driven by ATP hydrolysis.

In another embodiment of the present invention, the rotation of the molecular motor is driven by convertible transmembrane electrochemical potential gradient. The transmembrane electrochemical potential gradient is converted from light energy or chemical energy.

In another embodiment of the present invention, the rotation speed of the molecular motor is regulated by combining the subunit of $F_0F_1$-ATPase with the antibody of β subunit (primary antibody), and optionally, further with a secondary antibody (an IgG specifically recognizing the primary antibody).

The present invention further provides the use of the molecular motor micropower biosensor for detecting biological macromolecules, viral molecules, etc., which comprises the steps of:

(1) combining the molecular motor micropower biosensor according to anyone of claims 1-7 with the antibody of a specific biological macromolecule or a viral molecule antigen;

(2) contacting the molecular motor micropower biosensor obtained from step 1 with a sample to be tested;

(3) comparing the fluorescence intensity between the molecular motor biosensor obtained from step 2 and a molecular motor micropower biosensor having not been contacted with a sample to be tested, under light excitation.

In one embodiment of the present invention, the molecular motor micropower biosensor combines the antibody of the specific biological macromolecule or viral molecule antigen through β subunit antibody-biotin-streptavidin anti biotin-biotin.

The molecular motor micropower biosensor of the present invention is highly sensitive and regulable. After subjected to appropriate modification (e.g., combining with antibodies of a specific biological macromolecule or a viral molecule antigen), the biosensor can detect target biological macromolecule or viral molecule in single molecule level. Hopefully, the molecular motor micropower biosensor of the present invention will be developed into a new generation of micropower single molecule sensor. It will step up the manufacture technologies of biosensor and nanomaterial into a higher lever, and promote revolutionary development in a variety of industries such as biochips, biopharmaceuticals, national defense, environment, energy, and information. The biosensor of the present invention can be applied to many fields and will generate massive economic and social benefits.

BRIEF DESCRIPTION OF DRAWINGS

The present invention will be further discussed in detail with reference to drawings and examples. Nevertheless, the following description is included for illustrative purposes merely and is not intended to limit the scope of the invention.

ATPase within the immunological sensor on clenbuterol hydrochloride detection over time. Curves (b), (c), and (d) show the results of the assays with $10^{-15}$ g/L, $10^{-13}$ g/L, and $10^{-11}$ g/L of clenbuterol hydrochloride, the culture time of which is 30 minutes and the culture temperature of which is 35° C.

MODE FOR CARRYING OUT THE INVENTION

The following examples are provided for illustrative purpose only, and should not be construed as limiting the present invention in any way.

EXAMPLE 1

The Assembly of Adjustable Molecular Motor Micro Power Biosensor

As shown in FIG. 4, the molecular motor micropower biosensor was assembled.

(1) Preparation of the Photosynthesis Complex (Chromatophores) of the Molecular Element.

Culturing photosynthesis bacteria (*R. capsulatus, I* 20, available from the cell bank of Institute of Microorganism, Chinese Academy of Science, (Accession number 1.2359)). Culture medium: $KH_2PO_4$, 1.0 g, $MgCl_2$ 0.5 g, $CaCl_2$ 0.1 g, NaCl 1.0 g, sodium acetate 1.0 g, sodium succinate 1 g, yeast extract, 1.0 g, $NaHCO_3$ 0.5 g, peptone 0.5 g (OXOID Great Britain), trace elements 1.0 ml, vitamin solution 1.0 ml, distilled water 1.0 L, pH 6.8, 8 pounds, autoclaved for 30 minutes. Components in the vitamin solution: biotin 0.1 g (Imported), nicotinic acid 0.35 g, Thiamine dichloride 0.3 g, Ca-panthothenate 0.1 g, Vitamin $B_{12}$, 0.05 g, Pyridoxolium Hydrochloride, Fluka 0.1 g, distilled water 1.0 L; components of the trace elements: $FeCl_2$ $4H_2O$ 1.8 g; $CoCl_2$ $6H_2O$ 0.25 g; $NiCl_2$ $6H_2O$, 0.01 g; $CuCl_2$ $2H_2O$ 0.01 g, $MnCl_2$ $4H_2O$ 0.07 g; $ZnCl_2$ 0.1 g, $B_3PO_4$ 0.5 g, $Na_2SeO_35H_2$ 0.01 g, $NaMoO_4H_2O$ 0.03 g, distilled water 1.0 L) temperature 30-35° C. Harvest: culture temperature of the bacterial was 28° C.; the bacteria were cultured under light (4,000 Lx) for 5-7 days, and collected by centrifugation at 5000 g. Chromatophores isolation: Sample was washed once by TS buffer (50 mM, Tricine (tri-(hydroxymethyl) methyl glycine, Imported from Amresco), pH 8.0, 0.25 M saccharose; 5 mM $MgCl_2$), followed by adding 15 ml of TS buffer. The pellet was resuspended, into which added 1 mg/ml of lysozyme (Imported form Sigma). The solution was incubated in ice for 30 minutes, and then subjected to ultrasonification (20% amplitude, Cole Parmer CPX 600 ultrasound machine 13# probe head, KQ218 type ultrasound machine manufactured by Kunshan City Ultrasound Machine Company) for 10 minutes, followed by centrifuging at 25,000 g. The supernatant was collected and centrifuged under 4° C. at 180,000 g for 90 minutes, and the resultant precipitation was chromatophore, which is a complex containing a molecular motor $F_0F_1$-ATPase and a multiple of light converting carrier (reference marks 3 and 9 in FIG. 2).

(2) Unidirectional Labeling of Fluorescence Probe (Extracellular Fluorescence Label)

Fluorescence was added into the above complex (commodity number: F-362 Molecular probe fluorescein DHPE (fluorescein-phospholipid)) to obtain extracellular fluorescence emitter. The rest of them were washed off by centrifugation (10000 g/30 min, 4° C.).

(3) Light Energy Conversion Device

The device is composed of biological and chemical molecule composite material, for instance, composed of LHIRC (light reaction center and composite) and cold light source.

(4) Supporting Material and Bilayer Lipid Fixation

Solid surface (such as glass) was coated with poly-lysine, followed by being linked with biotin-ACs-sulfo-Osu (Dojindo, Japan) and then streptavidin antibiotin. The bilayer lipid membrane contains lipid-biotin, (PE-biotin (product of Avidin Company). After being dissolved in ethanol (1 mg/mL 2 μl), it was added into the bilayer lipid membrane (20 mg/ml) and centrifuged 2-3 minutes later at 10,0000 g for 30 minutes. Sample containing the bilayer lipid membrane having lipid-biotin was linked to streptavidin antibiotin on the solid surface. When needed, the primary antibody of β subunit binds specifically to β subunit of $F_1$-ATP motor, and another IgG (goat-anti-rabbit, Sigma, Imported) secondary antibody can specifically recognize the primary antibody. Thus, a pair of molecular motors were constructed, the load difference between which is only of three molecules (three β subunits).

Thus, the setup of the molecular motor micropower biosensor of the present invention is completed.

EXAMPLE 2

Fluorescence Signal of the Molecular Motor Micropower Biosensor without Load (1) Detecting Method of the Sensor The sample was placed onto a glass surface or into a fluorescence well (1 ml) (Hitachi apparatus, type F-4500). The sample was exited at 488 nm, with emission wavelength of 520 nm. When the sample was initiated with 2 mM ATP (Sigma company), the molecular motor of the present invention will transport the protons from the external to the internal of the cell. As a result, $F_1$ rotated in counter-clockwise, increasing the extracellular pH from 8.0 to 9.0. At this time, the signal can be recorded conveniently by fluorescence probe Lipids-fluorescein located outside (or inside) of the cell membrane. If the molecular motor was loaded with different weight of loads (e.g., loaded with one antibody), its rotation speed will change significantly, which can be conveniently recorded by fluorescence probe Lipids-fluorescein (or fluorescein) located outside (or inside) of the cell membrane.

(2) The Prove of Counter-Clockwise Rotation of $F_1$ without Load

According to the working mechanism of the molecular motor, $F_0F_1$-motor is a reversible machine. When ATP is hydrolyzed into ADP and Pi, the three β subunits are in three different conformations, which drive γ subunit to rotate in counter-clockwise companied by influxing of protons from the outside of the cell. Conversely, when protons were transported across the membrane, they drove $F_1$ to rotate in clockwise through $F_0$, while synthesizing ATP from ADP and Pi, functioning as the "currency" in life process. Accordingly, when ATP was hydrolyzed into ADP and Pi, companied by the outflux of protons, the pH in the liquid environment will change. Furthermore, when the revolutions of $F_1$ in counter-clockwise direction increase, so will the fluorescence value.

In addition, the ATPase inhibitors will also influence the rotation of the molecular motor, as well as the fluorescence value (unless specified otherwise, the fluorescence probe Lipids-fluorescein labeled outside was used to exemplify the present invention, as shown in FIGS. 6*a*, 6*b*, and 6*c*).

The detection principle of the biosensor used to detect molecular motor rotation can be seen from FIGS. 6*a*, 6*b*, and 6c: the rotation speed of the molecular motor is related directly to $F_0F_1$ molecular motor. FIG. 6a indicates that the fluorescence intensity is directly related to pH value. FIG. 6b shows that the fluorescence intensity change is related to the concentration of $Na_2SO_3$. FIG. 6c shows the influences of different ATPase activators and inhibitors on the fluorescence intensity changes, wherein NaN3 is an inhibitor of $F_1$-ATPase; PNP-AMP is an inhibitor of $F_1$-ATPase; DCCD (dicyclohexylcarbodiimide) is an inhibitor of $F_0$ ion channel. Therefore, all of the above major inhibitors can inhibit $Na_2SO_3$ activation and are related to proton channel, indicating the unidirectional labeled fluorescence probe and the $F_0F_1$-ATP motor can be used as the biosensor of $H^+$-ATPase ion channel (molecule motor).

Figure 1:
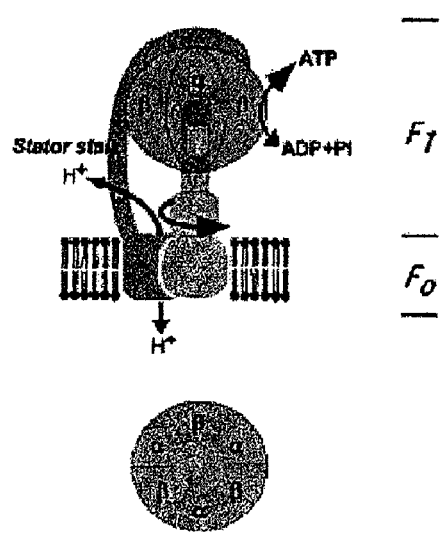
FIG. 1 shows the major components of the $F_0F_1$-ATP molecular motor.
Figure 2:
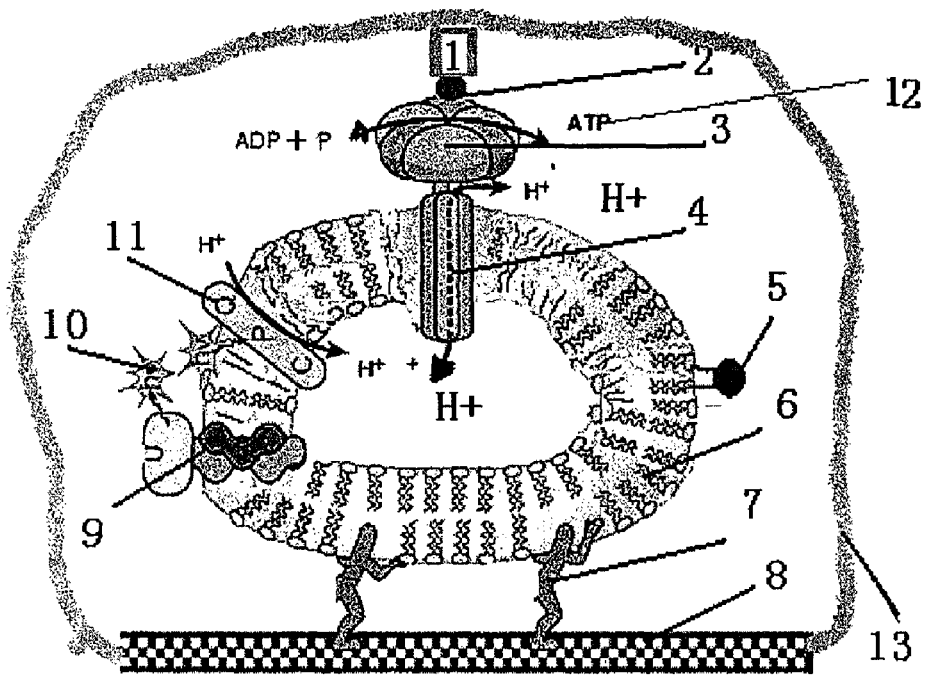
FIG. 2 is a schematic view of the molecular motor micropower biosensor of the present invention (1: sample to be tested (antigen); 2: antibody of the β subunit; 3: $F_1$-ATP motor; 4: $F_0$-ATP motor; 5: signal molecule (fluorescence probe); 6: bilayer lipid; 7: support; 8: solid surface; 9: light energy conversion device; 10: light energy emitting device; 11: electron conversion device; 12: power source ATP/ADP and $H^+$; 13: packaging of the micro reactor (such as 96-well plate, sample well and cover of fluorescence, etc)
Figure 3:
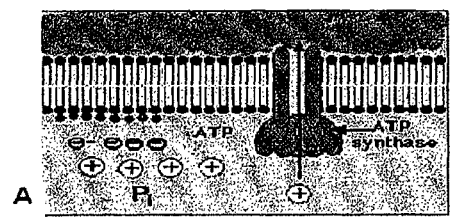
FIG. 3 shows the relationship between Lipids-fluorescein signal and the rotation of $F_1$-ATPase molecular motor (the coupling between $H^+$ concentration/fluorescence signal unidirectional labeling inside the cell and the rotation of the molecular motor; A: before ATP hydrolysis; B: after ATP hydrolysis; red dots in the figure represent unidirectional labeling of the fluorescence molecule.
Figure 3:
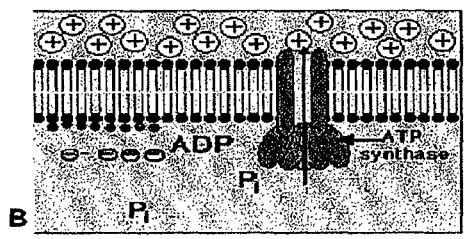
Figure 3:
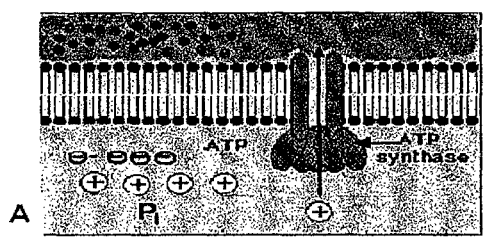
Figure 3:
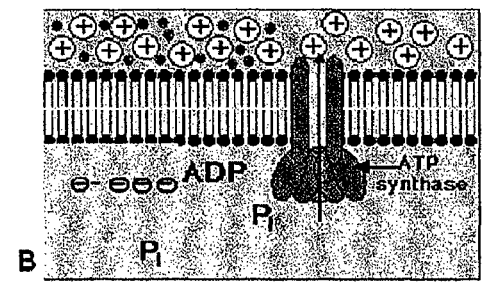
Figure 4:
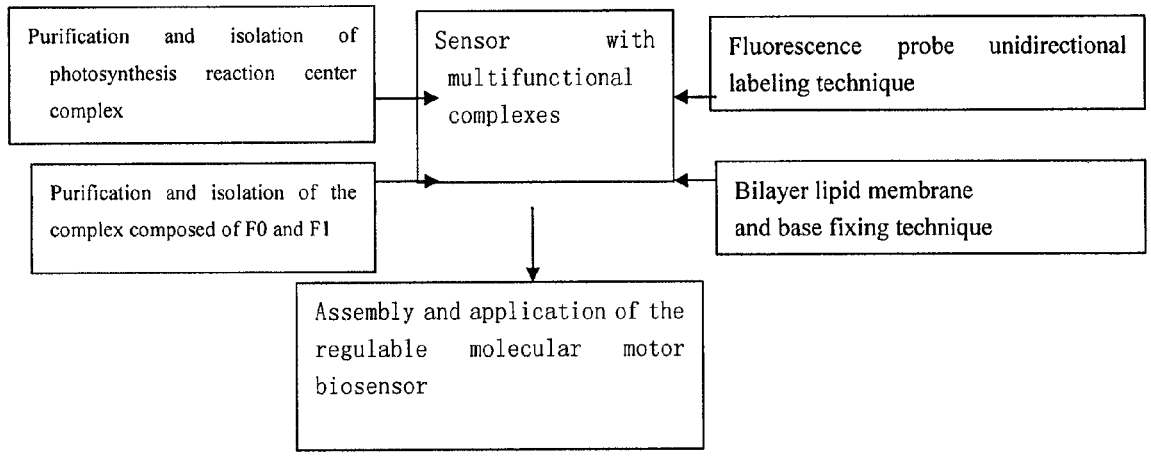
FIG. 4 shows the setup and working mechanism of the regulable molecular motor micropower biosensor.
Figure 5:
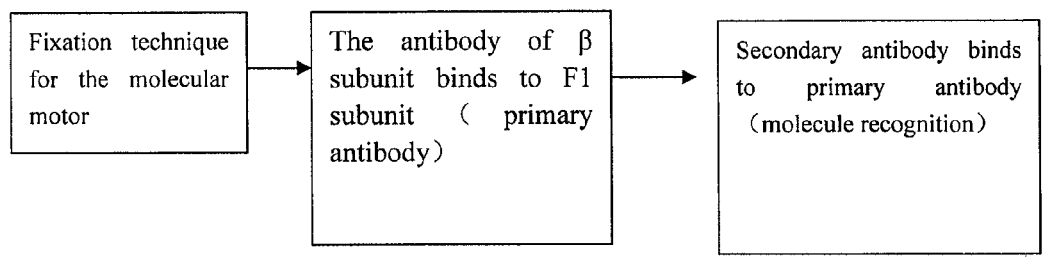
FIG. 5 shows the process of testing a sample.
Figure 6:
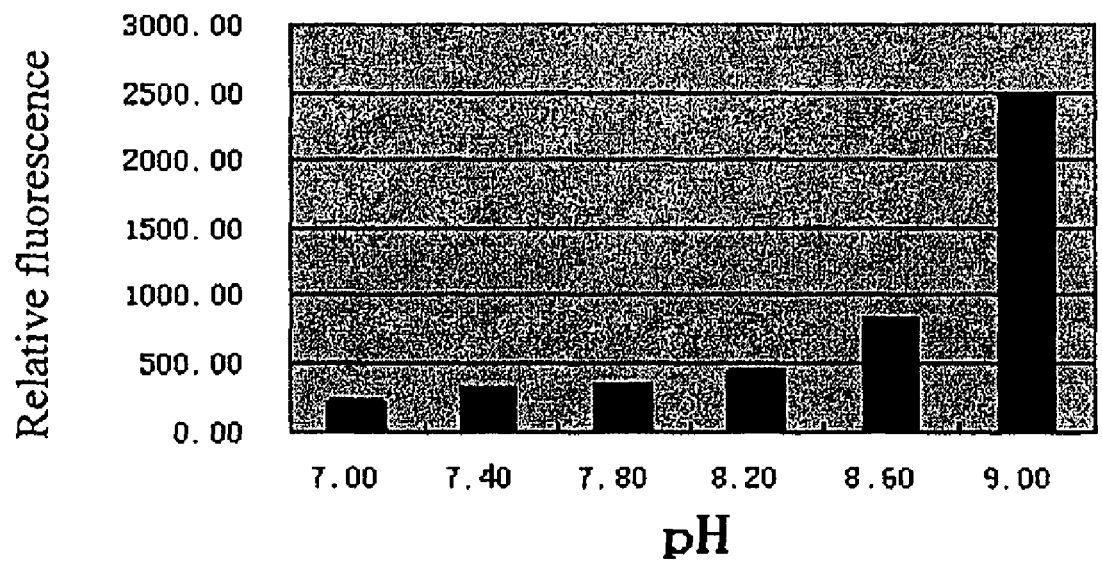
FIG. 6a shows the relationship between the fluorescence intensity of the external fluorescence labeling and pH value.
FIG. 6b shows the relationship between the fluorescence intensity of the external fluorescence labeling and the concentration of $Na_2NO_3$.
FIG. 6c shows the relationship between the fluorescence intensity of the external fluorescence labeling and different inhibitors.
FIG. 6d shows the fluorescence intensity of the internal fluorescence labeling and pH value (from left to right, the pH values in 0.1 mM Tricine buffer system are 4.2; 5.0; 5.4; 6.0; 6.4; 7.0; 7.4; 7.8; 8.2; and 8.6, respectively).
Figure 6:
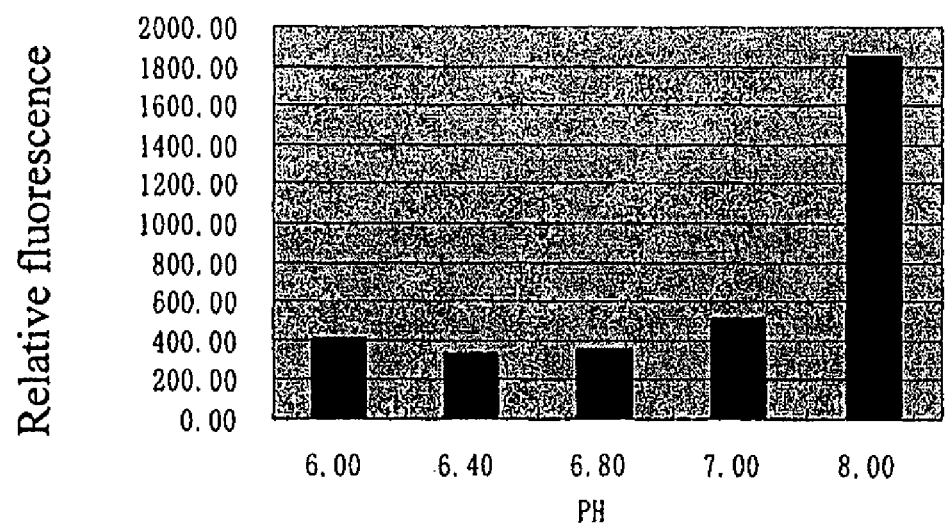
Figure 6:
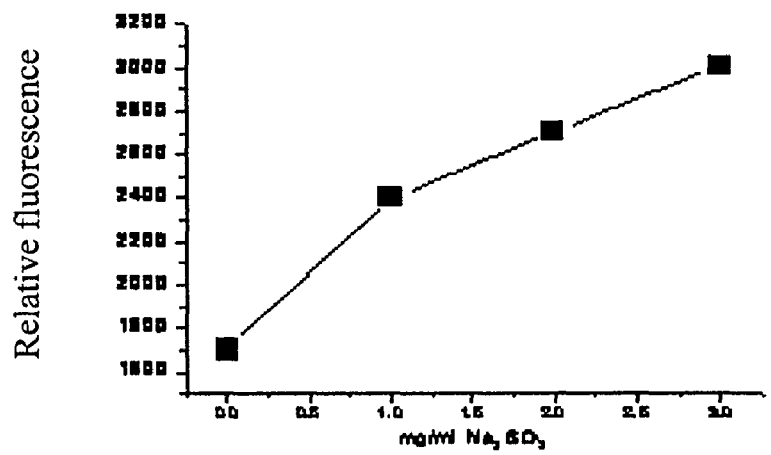
Figure 6:
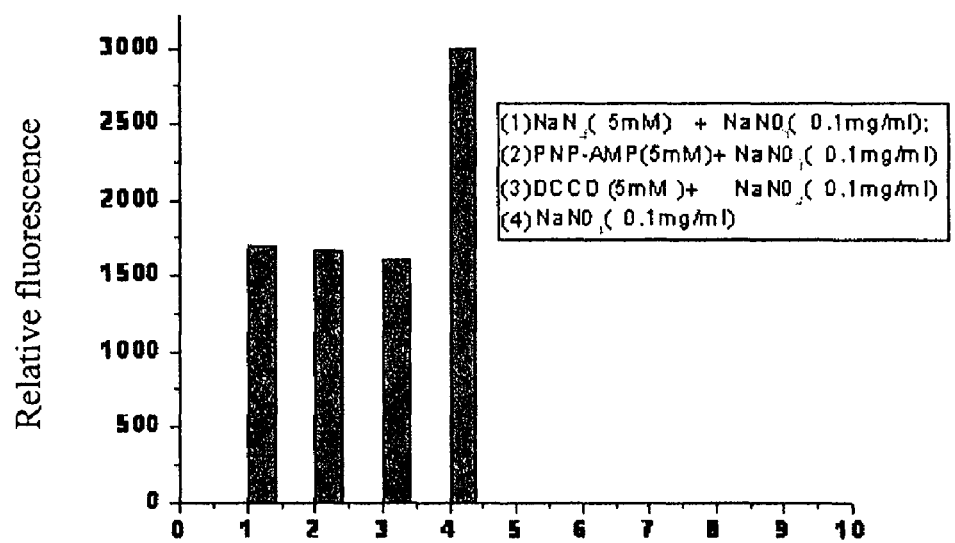
Figure 6:
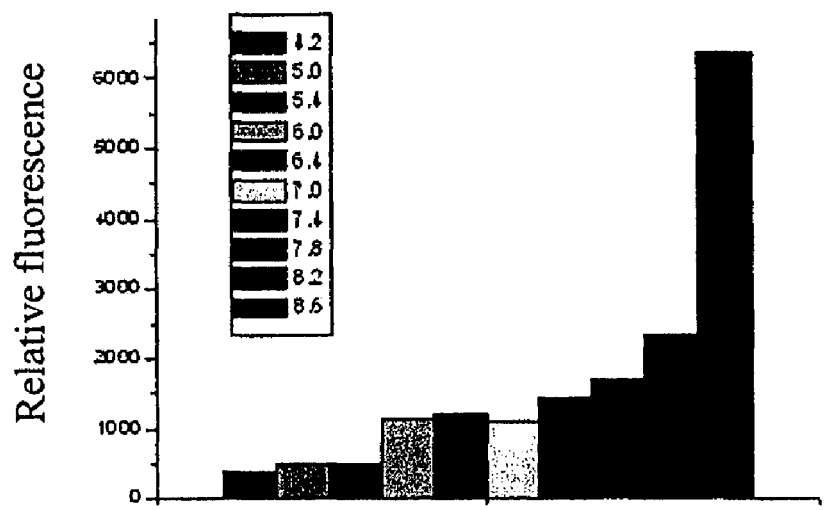

When inner labeled fluorescein was used, a similar result was achieved, as shown in FIG. 6d.

EXAMPLE 3

Fluorescence Signal of Molecular Motor Micropower Biosensor with Different Load

Preparation of the Antibody of the β Subunit: the Expression of Thermophilic Bacteria Bacillas PS3 and the purification of β subunit were carried out according to literatures (*Science Reports*, 2004, (13)1342-1347). The purified p subunit was emulsified with adjuvant in 1:1 before inoculation. The β subunit was inoculated at multiple spots on the dorsal of a 250 g rabbit (initially injected with 1 ml once every two weeks). One month later, the immunization was boosted 1-2 times to obtain polyclonal antibodies.

Based on the molecular motor micropower biosensor setup in Example 1, the β subunit primary antibody specifically bond to the β subunit of $F_1$-ATP motor. Another IgG (goat-anti-rabbit, Sigma, Imported) secondary antibody can specifically recognize the primary antibody of the β subunit, thus completing the setup of a pair of molecular motors, the load difference between which is only of three molecules (three β subunits).

Figure 7:
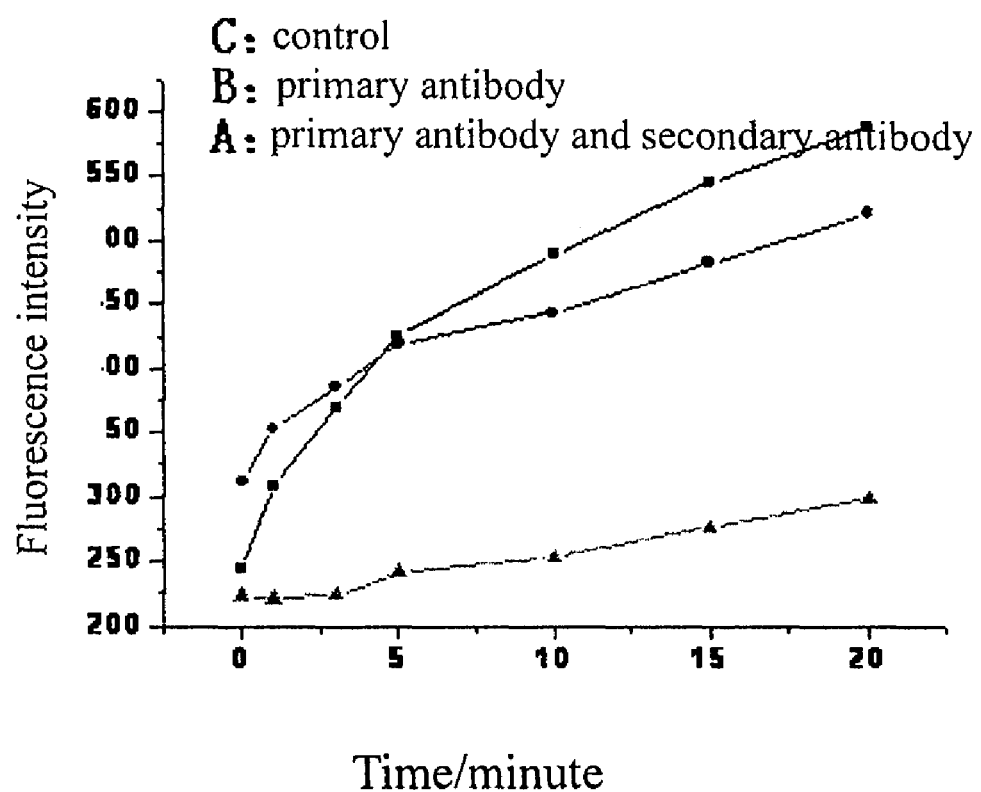
FIG. 7a is a diagram showing the rotation speed changes of $F_0F_1$-molecular motor with different loads (C: control, transporting 120 $H^+$/sec (calculated value); B: 60 revs/sec, after loaded with primary antibody; A: 12 revs/sec, after loaded with primary antibody and secondary antibody) (A, B, and C, arranged in order from top to bottom)
FIG. 7b is a histogram showing the rotation speed changes of $F_0F_1$-molecular motor with different loads.
Figure 7:
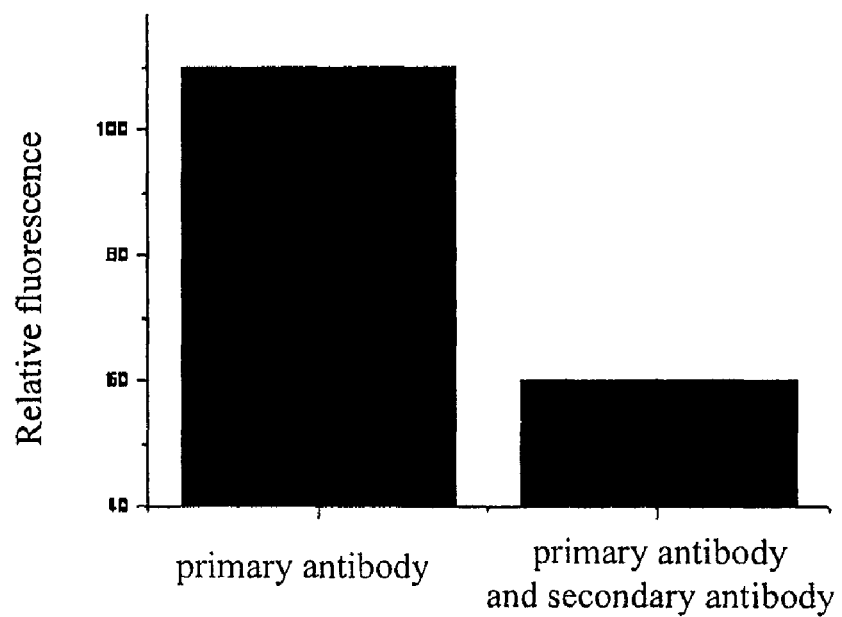

According to the detection method described in Example 2, the fluorescence signal of the molecular motor micropower biosensor with different loads (as shown in FIGS. 7a and 7b). The method of calculating the average rotation speed of the molecular motor is as follows: the sample was placed into a capillary with a length of 20 µl and a diameter of 0.289 mm (micropipets vwr, product of Scientific Company), which was then centrifuged at 15,000 revs/90 min, with a compacting volume ratio of 2.5:38; the cell number in 1 µl solution is $1.2 \times 10^{12}$, with a diameter of 60 nm. When the concentration and volume of the sample and the pH changes are known, the average rotation speed can be calculated (number of $H^+$ transported/second). ($C=F^2/2.3RTX\beta$, wherein $\beta=-\Delta[H^+$ in total$]$/pH, Biophysical Journal, (86), 2004, 4094-4109).

FIG. 7b further indicates that when the molecular motor is linked to different loads such as primary antibody or primary antibody and secondary antibody, both its rotation speed and the fluorescence intensity will vary significantly. Therefore, the rotation of the molecular motor can be regulated by changing the loads of the molecular motor.

EXAMPLE 4

Figure 8:
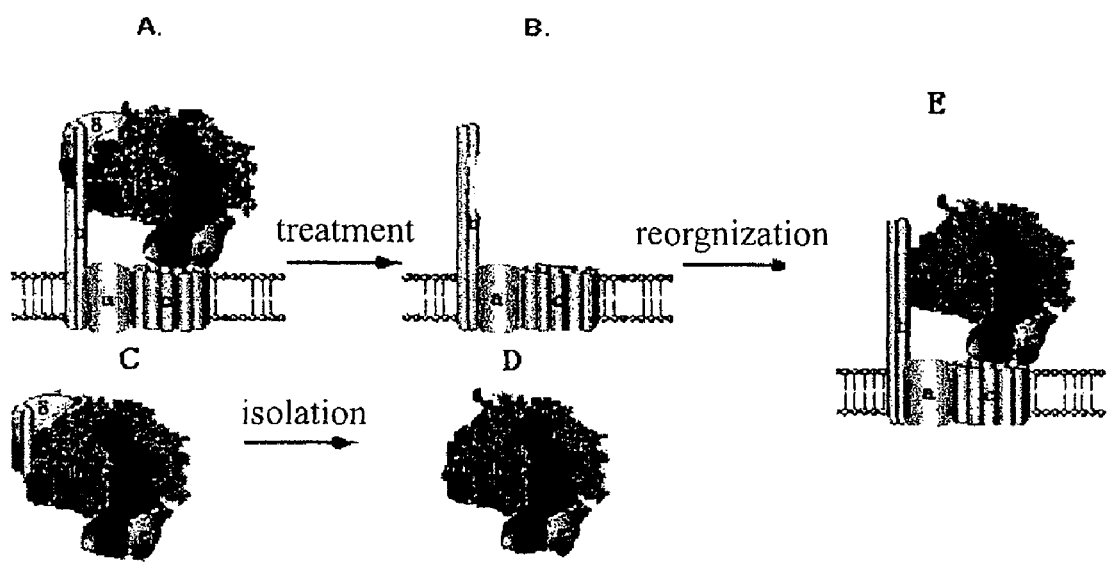
FIG. 8 is a mode chart showing light initiated rotation (mode chart of $F_0F_1$ during setting up the system; A represents the complete $F_0F_1$; B indicates that $F_0F_1$ lost $F_1$-ATP subunit after being treated with EDTA (10 mM); C indicates a complete $F_1$ was obtained after centrifugation; D indicates a $F_1$ without δ subunit; E represents a $F_0F_1$ molecular motor rotation experimental setup obtained by the combination of a $F_0$ and a $F_1$ without δ subunit.
Figure 9:
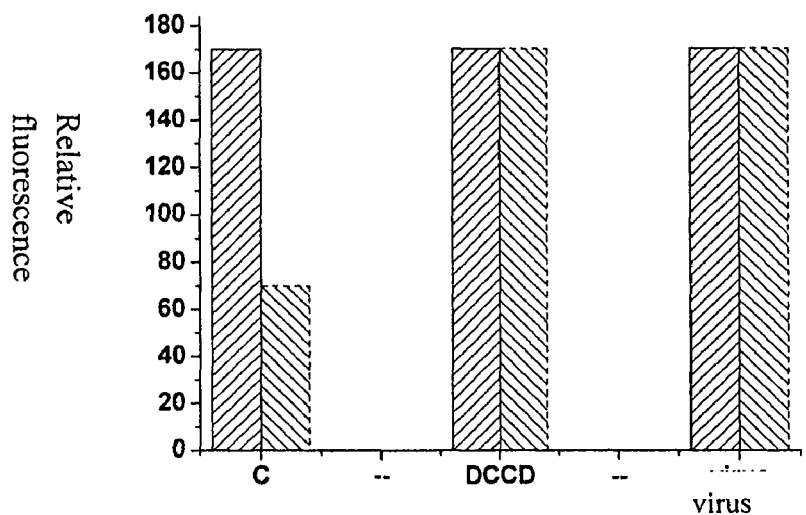
FIG. 9 is an experimental schematic view showing a method of using light initiated rotation of $F_0$-c-$F_1$ motor to specifically detect viruses.
Figure 10:
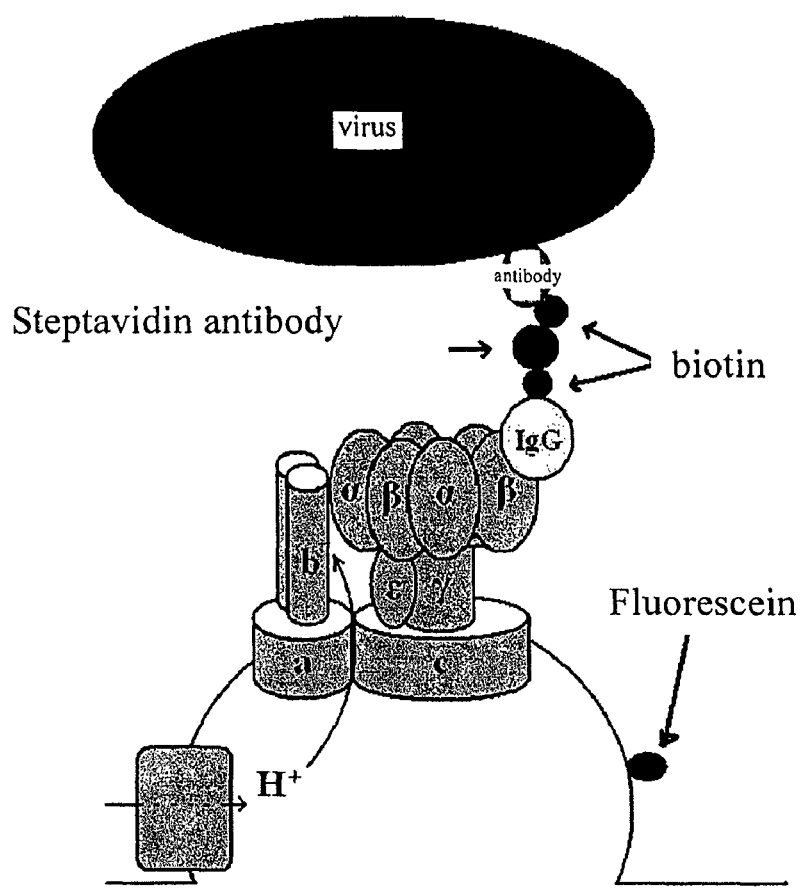
FIG. 10 shows a method of using light initiated rotation of $F_0$-c-$F_1$ motor to specifically detect viruses.

Light Excited Molecular Motor Rotation and Virus Specific Detection by the Molecular Motor In order to prove that light excitation can drive the rotation of the molecular motor, light was used to excite proton transport across the membrane, which in turn initiated $F_0$ and regulated the rotation of $F_1$. The rotation speed changes were detected under different loads. The structure of $F_1F_0$-ATP molecular motor was modified as in FIG. 8.

The material used is δW28L expressed by bacterium pSWM92/DK8. $F_1$ is a generous gift from A. E. Senior Professor (University of Rochester, medical center). The purification of $F_1$ and the removal of δ were carried out according to Senior: Jaachim Webber, Susan Wilke, Mount, and Alan E. Senior, Quantitative Determination of Binding affinity of Subunit in *E. Coli*, F1-ATPase, J. B. C. 272(21):18390-18396 (2002). After hybridizing with chromatophores without $F_1$, the sample was stored at −20° C.

Lacking δ subunit in the experimental system, ATP can not be synthesized during the process of $F_0$ rotation and coupling to $F_1$ initiated by proton gradient, rather, the energy of the proton gradient was transferred to $F_1$ to initiate rotation (the purpose of adding $NaN_3$ and ATP is to inhibit ATP hydrolysis). Cross-membrane gradient was developed when light (for 20 minutes, with a wavelength of above 550 nm) initiated electron transfer in photosynthesis bacteria, coupled with proton influxing. When light was removed, the cross-membrane gradient initiated the rotation of Fc and $F_1$-a3β3γ,ε, which is directly related to the loads on $F_1$. β subunit of $F_1$ was linked to the antibody of the avian influenza virus (pre-bonded with biotin) with streptavidin-biotin-primary antibody.

Other viral molecules (avian influenza virus (H9): antibody was provided by Harbin Veterinary Institute, the preparation and purification of the avian influenza virus sample were carried out according to literatures (*Animal Virology*, Science Publishing house, (1997) edited by Yin Zhen, Liu Jinghua et. al.), pre-linked with biotin, adding the $F_0F_1$ ATP motor-biotin-streptavidin antibiotin-biotin-virus system (see FIG. 10), observing fluorescence signal: using opton Axiovert 405M, inversion fluorescence microscopy, CCD Princeton instrument company, Model: RTE/CCD-782, image enhancerG2 II 18/18 produced by XiAn Institute of Precision Optics, Chinese Academy of Sciences.

As shown in FIG. 9, the fluorescence intensity of C (control) decreased about 30% after 10 minutes, which indicates $F_0$ drove $F_1$ to rotate and protons outfluxed at the same time, thereby reducing the fluorescence intensity of the system; DCCD: 2 mM DCCD was added into the system to block the proton channel of $F_0$, and in such case, no fluorescence intensity difference was observed after 15 minutes; Virus: avian influenza virus H9 (obtainable by conventional method), the antibody of the avian influenza virus firstly bond to biotin and then to the streptavidin antibiotin on the antibody of the β subunit. The redundant biotin was washed off. After the antibody of the avian influenza virus specifically bond to the avian influenza virus, PBS was used to wash off the unbound part. At this time, although the protons still outfluxed from the inside, the loads on $F_1$ cause the rotation speed of $F_1$ to decrease, thus regulating the transport of the proton channel of $F_0$. At this time, no fluorescence intensity change was observed. Therefore, $F_1$ rotation initiated by light excitation is directly related to its loads (the average value of 10 samples used in the above experiments). This example demonstrated that the molecular motor micropower biosensor of the present invention can be used to detect virus and macromolecule in single molecule level.

EXAMPLE 5

Fluorescence Probe Labeled to Inner Chromatophore and its Application Mechanism Previously, the application of the chromatophore where fluorescence probe was labeled to its outside was described. From now on, the application of the chromatophore where fluorescence probe (F1300) was unidirectional labeled to its inside will be described in detail. Method of inside labeling: 3 μl F1300 fluorescence probe (0.0015 mol/L, dissolved in ethanol) was added into 150 μl chromatophore, which was then ultrasonicated at 4° C. for 3 minutes to make fluorescence probe enter the chromatophore. The outside fluorescence probe was centrifuged at 12000 rpm for 30 min under 4° C., and washed for three times. At the same time, it was further found that the weight of the loads on β subunit can regulate the synthesis activity of $F_1F_0$-ATPase. Loads of small molecule weight down-regulated the activity, but there was a rebound with the increase of the loads, i.e., when the molecular weight of the load was increased to a certain value, the synthesis/hydrolysis activity of the $F_1F_0$-ATPase was up-regulated. Since the molecular weight of the load on β subunit was used to regulate the synthesis/hydrolysis activity of the $F_1F_0$-ATPase, and since fluorescence probe was pre-labeled to the inner chromatophore, the system containing the molecular motor fixed therein can be conveniently used as a sensor. During ATP synthesis, since proton outfluxed and since the fluorescence probe (F1300) was labeled to the inner membrane, the fluorescence signal increased with proton outfluxing. When molecular weights of the loads on $F_1F_0$-ATPase are different, the regulation of the synthesis activity of the $F_1F_0$-ATPase and the coupling of $F_0$-ATP proton transport speed can be indicated by the fluorescence signal of the fluorescence probe.

(1) Fluorescence Probe Labeled to Inner Chromatophore and the Results.

Figure 11:
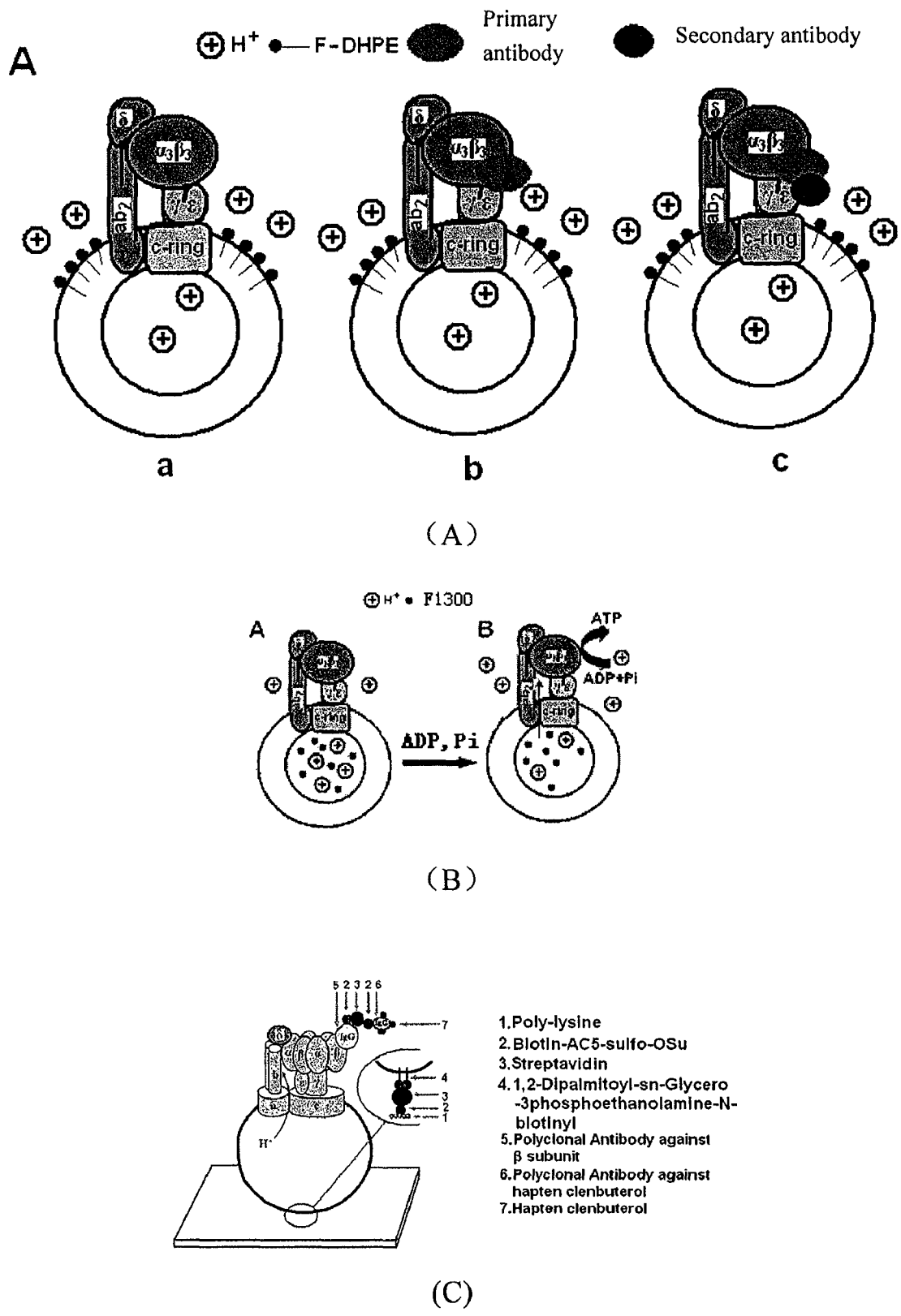
FIG. 11A shows the basic mechanism of the application of ATP molecular motor as an immunological sensor during ATP hydrolysis (fluorescence probe was labeled outside the membrane): (a) basic setup; (b) linked with β antibody; (c) linked with a recognition molecule.
FIG. 11B shows the application of ATP molecule motor as an immunological sensor during ATP hydrolysis (fluorescence probe was labeled inside the membrane): (A): fluorescence probe is labeled inside chromatophore; (B): Adding ADP to initiate ATP synthesis.
FIG. 11C is a schematic view of the mechanism of using molecular biosensor to detect clenbuterol hydrochloride.
Figure 12:
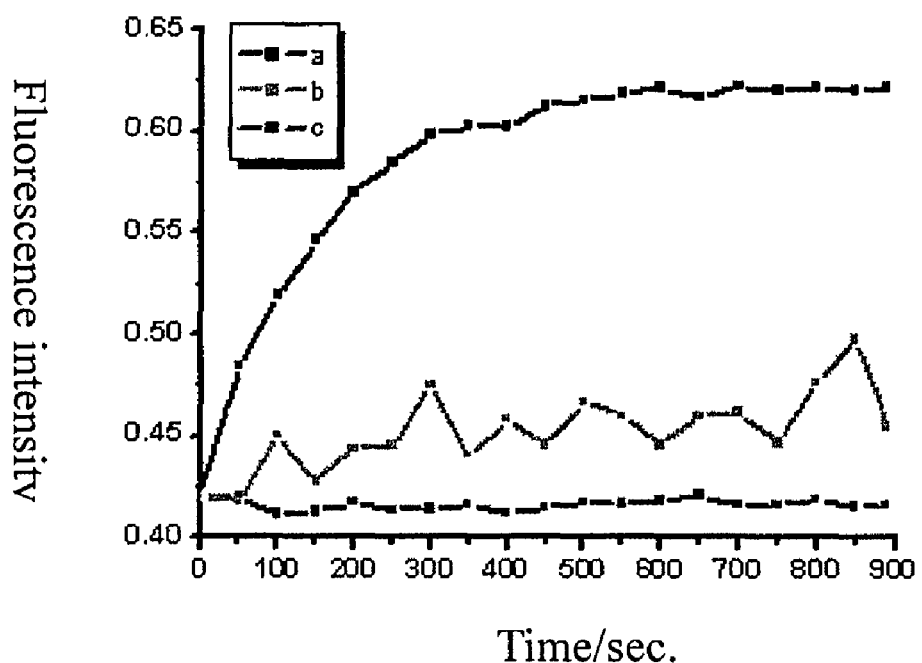
FIG. 12 shows the relationship between fluorescence dynamics curve and $F_0$-proton transport (a, b, and c, arranged in order from top to bottom). Curve a: control; curve b: the same as (a) except DCCD was added; curve c: no ADP was added.

FIG. 11B is a schematic view of the fluorescence labeling. Using method similar to those in Examples 1 and 2, a complex of Chromatophore inner labeled with fluorescence was immobilized on the surface of a 96-well-plate. During ATP synthesis, the fluorescence signal increased over time. The result is shown in FIG. 12. Curve a: control; curve b: with the addition of DCCD; curve c: no ADP was added to initiate reaction. The result indicates when inner labeled chromatophore complex was immobilized on the 96-well-plate, the fluorescence signal can reflect the process of proton transport. The experiment can be performed on a 96-well-plate or a culture dish under the observation of a fluorescence microscopy. FIG. 12 indicates the chromatophore inner labeled with F1300 fluorescence probe can be used as proton transport indicator during ATP synthesis.

(2) The Application of the Result of 96-Well-Plate Fluorescence Experiment in Virus (Avian Influenza Virus, H9) Detection.

Figure 13:
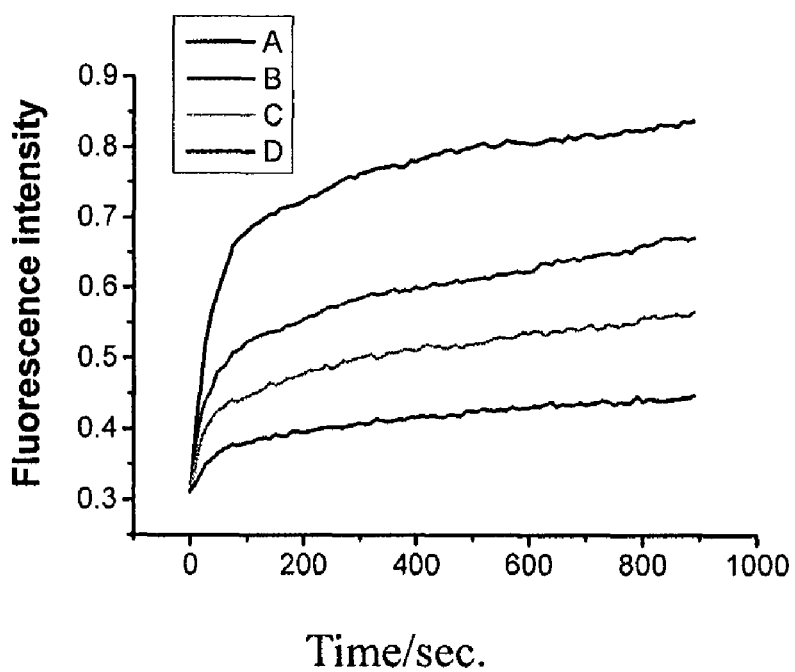
FIG. 13 shows the application of the biosensor in virus detection (avian influenza virus, H9), wherein F1300 fluorescence probe was labeled inside chromatophore, which was fixed to the surface of a 96-well-plate (a, b, c, and d, arranged in order from top to bottom). When β subunit of $F_1F_0$-ATPase carries molecules with different weight, it will cause changes in fluorescence map dynamics curve. Curve b: control; curve a: β subunit loaded with the antibody of β subunit and its secondary antibody; curve c: β subunit loaded with the antibody of β subunit; curve d: β subunit loaded with the antibody of β subunit and its secondary antibody.

Using method similar to that in Example 4, the chromatophore system inner labeled with fluorescence probe was used to detect avian influenza virus H9. The result is shown in FIG. 13, where F1300 fluorescence probe was labeled to inner chromatophore, which was fixed to the surface of a 96-well-plate. The figure indicates that the change of fluorescence signal during ATP synthesis over time. It can be seen from FIG. 13, when β subunit of $F_1F_0$-ATPase carries molecules with different weight, it will cause changes in fluorescence map dynamics curve. Curve b: control; curve a: β subunit loaded with the antibody of β subunit and its secondary antibody; curve c: β subunit loaded with the antibody of β subunit; curve d: β subunit loaded with the antibody of β subunit and its secondary antibody. It can be seen from the comparison of curve b and curve d that $F_1F_0$-ATPase can be used as biosensor in chromatophore to detect viruses.

(3) The Result of 96-Well-Plate Fluorescence Experiment in Virus Detection Over Time.

Figure 14:
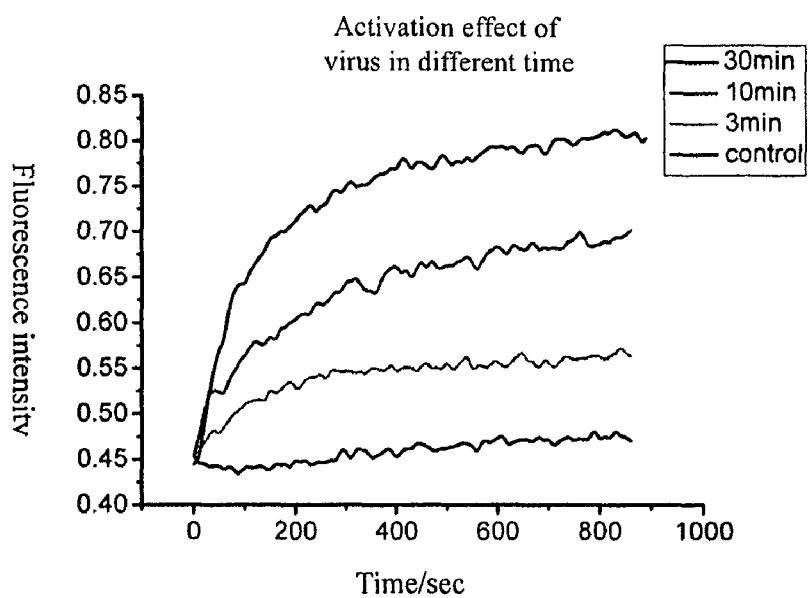
FIG. 14 shows the fluorescence experimental result of a 96-well-plate in virus detection (A, B, C and D, arranged in order from top to bottom). Curve A: a culture time of 30 minutes; curve b: a culture time of 10 minutes; curve c: a culture time of 3 minutes; curve d: a culture time of 0 minute.

In order to be used in a biosensor to detect viruses, the plate was monitored during the whole time course. FIG. 14 shows the fluorescence curve variation dynamics of the virus samples with different culture times (A-D, arranged in order from top to bottom). Curve A: a culture time of 30 minutes; curve b: a culture time of 10 minutes; curve c: a culture time of 3 minutes; curve d: a culture time of 0 minute. It can be seen that a culture time of 30 minutes reached the state of saturation, with the culture temperature of 25° C.

(4) The Application of Chromatophore System Inner Labeled with Fluorescence Probe in Single Molecule Sensor within a Microscopy System.

Figure 15:
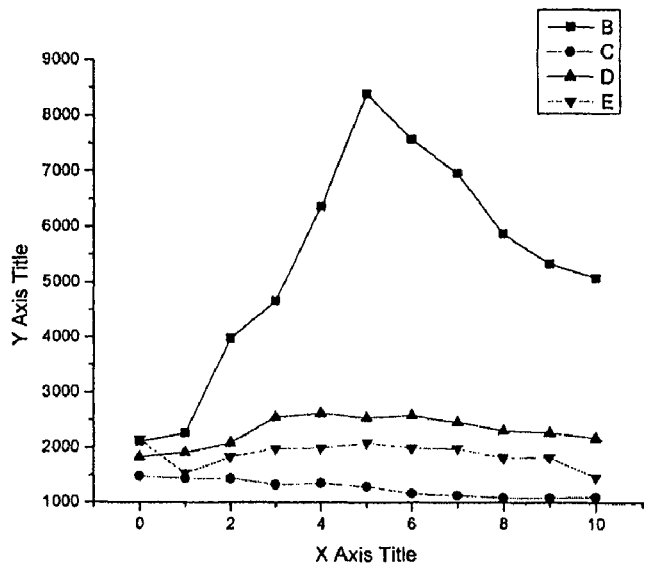
FIG. 15 shows the time course of a single molecule virus detection observed with a fluorescence microscope (B, C, D, and E, arranged in order from top to bottom). Curve b: ATP chromatophore molecule loaded with two antibody systems and virus molecules; curve c: ATP chromatophore molecule only; curve d: ATP chromatophore molecule loaded with two antibody systems; curve e: ATP chromatophore molecule, without adding ADP to initiate ATP synthesis.

In order to observe in a single molecule level, the study was carried out under a fluorescence microscopy oil image (100×). The result indicates (FIG. 15) that compared with control group, the changes of the molecular fluorescence signal loaded with the virus is much more significant. Curve b: ATP chromatophore molecule loaded with two antibody and virus molecules; curve c: ATP chromatophore molecule only; curve d: ATP chromatophore molecule loaded with two antibody systems; curve e: ATP chromatophore molecule, without the addition of ADP to initiate ATP synthesis. The result indicates (FIG. 15) that compared with control group, the changes of the molecular fluorescence signal loaded with the virus is much more significant.

(5) The Application of Chromatophore System Inner Labeled with Fluorescence Probe in Small Molecule Detection. (Clenbuterol Hydrochloride, Purchased from Sigma CO. (St. Louis, USA), Clenbuterol (4-amino-t-butylaminomethyl-3, 5-dichlorobenzyl Alcohol Hydrochloride)).

The chromatophore system inner labeled with fluorescence probe was used to detect small molecules. Clenbuterol hydrochloride was used herein to exemplify the present invention. The mechanism of using ultrasensitive molecular biosensor having immunological recognition function and molecular motor to detect clenbuterol hydrochloride is the same as that of virus detection.

The difference is that by using polyclonal antibody of clenbuterol hydrochloride as a specific recognition molecule, the mechanism is more clear and reliable (see FIG. 11C).

Figure 16:
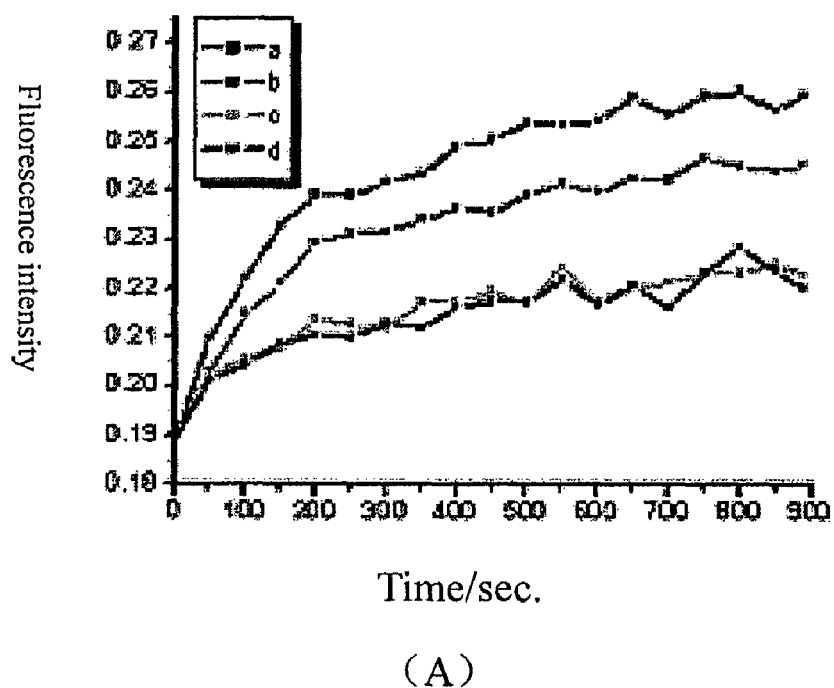
FIG. 16A shows the influence of the $F_1F_0$-ATPase within the immunological sensor on clenbuterol hydrochloride detection over time (a, b, c, and d, arranged in order from top to bottom). Curve a: a culture time of 30 minutes; curve b: a culture time of 10 minutes; curve c: a culture time of 3 minutes; curve d: a culture time of 0 minute; a culture temperature of 35° C.
FIG. 16B shows the influence of the $F_1F_0$-
Figure 16:
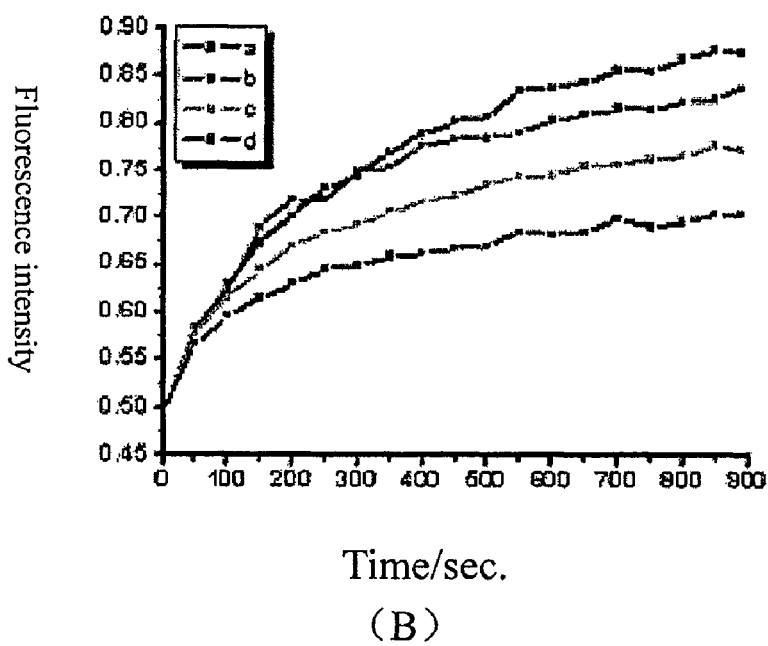

The results are shown in FIG. 16: FIG. 16A shows the time dynamics course of small molecule detection. Curve a: a culture time of 30 minutes; curve b: a culture time of 10 minutes; curve c: a culture time of 3 minutes; curve d: a culture time of 0 minute. It can be seen from the dynamics curve that basically a culture time of about 10 minutes can reach the state of saturation. FIG. 16B shows the control group. Curves (b), (c), and (d) show the results of the assays with $10^{-15}$ g/L, $10^{-13}$ g/L, and $10^{-11}$ g/L of clenbuterol hydrochloride.

It can be seen from the concentration curve that the detection sensitivity for clenbuterol hydrochloride is about $10^{-15}$ g/L, which is 10,000-100,000 times more sensitive and 30 minutes faster than those in the current conventional methods.

Major Steps in the Detection:

A. 1 μl fluorescence probe F1300 (0.00015 mol/l) was added into 100 μl chromatophore, followed by ultrasonication in ice for 3 min;

B. the resultant was diluted to 1 ml with Tricine-NaOH solution (0.1 mM Tricine, 5 mM $MgCl_2$, 5 mM KCl, pH 6.0), and centrifuged at 12,000 rpm for 20 min, followed by washed for 2-3 times to thoroughly remove the free fluorescence probes; the pellet was resuspended in 1 ml Tricine solution;

C. 0.1% chitosan was added into a 96-well nontransparent plate (Lab systems Cliniplate), 50 μl/well, and then left standing at 4° C. overnight;

D. decanting redundant chitosan, and added into each well 80 μl of fluorescence labeled chromatophore, and then left standing at 4° C. overnight;

E. gently removing unattached chromatophore, followed by washing 2-3 times with Tricine;

F. adding into each well 80 μl solution (50 mM Tris-HCl, 5 mM $MgCl_2$, 5 mM $K_2HPO_4$, 10% glycerol, pH 8.5) containing 2 mM ADP to initiate reaction;

G. at the same time, using fluorescence microplate scanner (Fluoroskan Ascent, Labsystems, Finland) to detect fluorescence intensity change over time (EX 485 nm, EM 538 nm, time interval: 50 s), with a detection time of 15 min.

Detection of Single Molecule Fluorescence:

80 fluorescence labeled chromatophores were added into each well of sample wells (Glass Bottom Dishes coated with poly-lysine were free samples from Matteck Company (U.S.A.), and left standing at 4° C. overnight. Unattached chromatophores were gently removed and washed 2-3 times by Tricine, with each time adding 80 μl of a solution (50 mM Tris-HCl, 5 mM $MgCl_2$, 5 mM $K_2HPO_4$ 10% glycerol, pH8.5) containing 4 mM ADP to each well to initiate reaction; fluorescence microscopy Olympus IX71, CCD camera (Princeton Instruments Inc, G2 II 18/18) was used to detect fluorescence intensity change over time (EX 485 nm, EM 538 nm, time interval: 50 s), with a detection time of 10 min.

It should be understood that many variations to those described above are possible. Since modifications and variations to the descriptions will be apparent to those of skill in this art after reading the invention, it is therefore intended that this invention be limited only by the scope of the appended claims.

What is claimed is:

1. A biosensor comprising:
    (a) a chromatophore, which comprises an $F_0F_1$-ATPase molecular motor;
    (b) a signal molecular output device comprising a light excitation and emission device and a fluorescence probe;
    (c) a power resource system comprising water, ATP, ADP, Pi, and visible light;
    (d) a protective layer comprising a bilayer lipid membrane;
    (e) a supporting material; and
    (f) a solid support, wherein the bilayer lipid membrane is attached to the solid support by the supporting material; wherein a β subunit of the $F_0F_1$-ATPase molecular motor is bound directly or indirectly to an antibody that specifically recognizes an antigen molecule, wherein binding of the antibody to an antigen changes a rotation speed of the molecular motor in a manner that can be detected by a change in fluorescence of the florescence probe.

2. The biosensor of claim 1, wherein the fluorescence probe is Lipids-fluorescein labeled outside the membrane.

3. The biosensor of claim 1, wherein the fluorescence probe is fluorescein labeled inside the membrane.

4. The biosensor according to claim 1, wherein rotation of the molecular motor is driven by ATP hydrolysis or synthesis.

5. The biosensor according to claim 1, wherein rotation of the molecular motor is driven by a transmembrane electrochemical potential gradient.

6. The biosensor of claim 5, wherein the transmembrane electrochemical gradient is converted from light energy or chemical energy.

7. A method for detecting a biological macromolecule or a viral molecule at a single molecule level, comprising the steps of:
    (1) combining the biosensor according to claim 1 with an antibody of a specific biological macromolecule or a viral molecule antigen;
    (2) contacting the biosensor obtained from step 1 with a sample to be tested;
    (3) comparing fluorescence intensity between the biosensor obtained from step 2 and a biosensor having not been contacted with the sample to be tested, under light excitation; wherein a change in the fluorescence intensity is indicative of the presence of said biological macromolecule or viral molecule.

8. The method of claim 7, wherein the biosensor binds to the antibody of the specific biological macromolecule or the viral molecule antigen through a β subunit antibody-biotin-streptavidin antibiotin-biotin.

* * * * *